United States Patent [19]
Tiffany

[11] Patent Number: 5,062,842
[45] Date of Patent: Nov. 5, 1991

[54] ISOTOPIC $CO_2$ LASER AND METHOD OF USE FOR MEDICAL TREATMENT

[75] Inventor: William B. Tiffany, Palo Alto, Calif.

[73] Assignee: Coherent, Inc., Palo Alto, Calif.

[21] Appl. No.: 454,139

[22] Filed: Dec. 21, 1989

[51] Int. Cl.$^5$ .............................................. A61N 5/06
[52] U.S. Cl. ........................................ 606/3; 606/10; 606/19; 128/395
[58] Field of Search ............................... 128/395–398; 606/31, 4–7, 10–19; 372/56

[56] References Cited

U.S. PATENT DOCUMENTS

| | | | |
|---|---|---|---|
| 3,769,963 | 11/1973 | Goldman et al. | 606/3 |
| 3,982,541 | 9/1976 | L'Esperance, Jr. | 606/4 |
| 4,550,240 | 10/1985 | Toida et al. | 606/11 |
| 4,559,942 | 12/1985 | Eisenberg | 606/14 |
| 4,583,539 | 4/1986 | Karlin et al. | 606/4 |
| 4,765,330 | 8/1988 | Bach | 606/7 |
| 4,917,084 | 4/1990 | Sinofsky | 606/7 |

OTHER PUBLICATIONS

"Use of Gas Jet Appositional Pressurization in Endosecopic Laser Photocoagulation", by Kimura et al; IEEE Trans on Biochem. Eng., vol. 25, No. 3, 1978, pp. 218–224.

The Handbook of Military Infrared Technology, William L. Wolfe (ed.), Office of Naval Research, Washington, D.C., 1965, pp. 227–237.

Irvine and Pollack, Icarus, vol. 8, No. 2, pp. 328–329, Mar. 1968.

"Runaway Selfabsorption in Muli-kilowatt $CO_2$ Lasers", Kay and Naylor, Applied Physics Letters, vol. 42, No. 3, Apr. 15, 1983.

"Extension of $CO_2$ Laser Wavelength Range with Isotopes", Jacobs and Bowers, Journal of Applied Physics, vol. 38, No. 6, p. 2692, May 1967.

"Determination of Laser Line Frequencies and Vibrational-Rotational Constants of $^{12}C^{18}O_2$, $^{13}C^{16}O_2$ and $^{13}C^{18}O_2$ Isotopes from Measurements of CW Beat Frequencies with Fast HgCdTe Photodiodes & Microwave Frequency Counters", Freed et al., J. of Molecular Spectroscopy, vol. 49, p. 439 (1974).

Primary Examiner—David Shay
Attorney, Agent, or Firm—Limbach, Limbach & Sutton

[57] ABSTRACT

A medical treatment laser is disclosed that minimizes absorption of laser energy along the beam path by using a lasing medium having a principal emission at a wavelength shifted from the absorption wavelength. In the preferred embodiment, a $CO_2$ laser filled with the $^{13}C^{16}O_2$ isotope is used. The $^{13}C^{16}O_2$ isotope generates a laser beam having a principal emission wavelength near 11.2 microns. The absorption of this wavelength in the conventional $CO_2$ purge and insufflation gases is quite small compared to the absorption of the 10.59 micron wavelength emitted by the standard $CO_2$ isotope. The difference in absorption allows the power generated by the laser to be maximally transmitted to the medical treatment site. In addition, the 11.2 micron line has a greater coefficient of absorption in human tissue, thereby enhancing surgery.

12 Claims, 1 Drawing Sheet

ISOTOPIC CO₂ LASER AND METHOD OF USE FOR MEDICAL TREATMENT

TECHNICAL FIELD

The subject invention relates to medical treatment laser systems and, more specifically, $CO_2$ laser systems.

BACKGROUND OF THE INVENTION

Recently, there has been a trend to utilize lasers in many medical applications. For example, some types of laser surgery are performed using carbon dioxide ($CO_2$) lasers. $CO_2$ lasers generate a principal wavelength of 10.59 microns which is absorbed in medical treatment predominantly by the water molecules in biological tissue. The absorption and conversion to heat of the laser energy in tissue allows the doctor to cut, cauterize, excise and perform other surgical procedures $CO_2$ lasers are also desirable because they can be designed to deliver relatively high power at low cost compared to other types of lasers.

The early $CO_2$ surgical lasers were of the flowing gas variety In these $CO_2$ systems, gas from tanks is continually flowed through the laser tube Since the early 1980's, sealed gas systems have been available as an alternative to flowing gas systems. While initially higher in cost, the sealed gas systems are less cumbersome to operate and do not require replacement of gas cylinders.

As is well known, another trend in surgery is to localize the intrusion into the body For example, knee surgery is much less traumatic using arthroscopic procedures This trend can also be seen where endoscopes have been modified to allow surgical procedures to be performed More specifically, endoscope were originally designed for viewing internal body parts. The endoscope consists of a cylindrical tube or sheath which can be inserted through a small incision or puncture in the body. It was recognized that if surgical tools could be manufactured to fit within the endoscope, entire surgical procedures could be performed without further invading the body of the patient. Since laser energy can be delivered along a narrow beam, significant effort has been expended to develop laser endoscopic surgical techniques.

One example of the combination of endoscopes and laser surgery is in laparoscopy procedures. In this procedure, an endoscope is inserted through a patient's abdominal wall. Laser light delivered through a laparoscope can be used to burn and remove lesions, adhesions or blockages, for example which might otherwise threaten life, cause pain, or inhibit the patient from becoming pregnant. In any endoscopic procedure using laser energy, it is typical that a purge gas is flowed through the endoscope to prevent smoke and burned tissue from moving up the endoscope and fouling optical elements. In laparoscopies, in addition to the purge gas, the doctor will also typically pump an insufflation gas into the patient's abdomen. The insufflation gas expands the abdomen away from the internal organs to provide a clearer view of the operating field. Where insufflation gas is used, it is even more important to provide a purge gas flow through the endoscope, because the positive pressure in the surgical area would otherwise force burned tissue and smoke into the endoscope, fouling the optics used to focus and deliver the laser beam.

Until a few years ago, a common purge and insufflation gas utilized by surgeons was nitrogen. Unfortunately, nitrogen had many undesirable side effects. For example, nitrogen is not readily flushed from the body and can produce bends-like symptoms in the patient or even disabling or fatal gas emboli in the circulatory system. Accordingly, the recent trend has been to use carbon dioxide ($CO_2$) as the purge and insufflation gas, because the circulatory and respiratory systems efficiently flush it from the body without complications.

It was recognized by those in the field that when carbon dioxide was used as the purge gas, a certain amount of the power from the $CO_2$ surgical laser would be absorbed by the purge gas. While room temperature $CO_2$ has an abundance of molecules in the ground state that will not absorb $CO_2$ laser light, there will always be a small but definite population of molecules having excited energy states, some of which correspond to the lower lasing level. This small percentage of molecules which populate the lower lasing level will absorb the photons of the $CO_2$ laser beam at the principal emission wavelength of 10.6 microns.

The absorption of $CO_2$ laser energy in $CO_2$ gas has been reported in other situations, particularly in long range communications through the atmosphere. For example, where a $CO_2$ laser beam is transmitted through the atmosphere over many miles, it will pass through enough atmospheric $CO_2$ even in low concentration that the absolute number of molecules in higher energy states will be sufficient to attenuate the beam to a significant level. However, this effect was not considered a problem in laser surgery because of the relatively short distances (a matter of inches or, at most, feet) across which the laser beam must traverse the highly concentrated $CO_2$ purge gas.

The applicant has discovered, however, that the absorption of laser energy by the purge gas can be much more acute than anticipated. In fact, the applicant has discovered that as the laser power is increased, the absorption of laser energy in the purge gas increases nonlinearly, and is caused by the phenomenon of thermal runaway absorption. Thermal runaway absorption has been previously observed in closed gas systems. In such systems, heat which is generated by the absorption of the laser light by the gas cannot be quickly dissipated, and, therefore, tends to heat the gas to a higher level. This heating will increase the population of energetic molecules. When the proportion of energetic molecules increases, the population of molecules in the lower lasing level capable of absorbing the $CO_2$ laser light increases. This in turn results in greater absorption of energy, greater heating and, again, greater absorption. This rapid cycle is termed "runaway". (See, for example, "Runaway Self-absorption in Multi-kilowatt $CO_2$ Lasers", Kay and Naylor, *Applied Physics Letters*, V. 42, No. 3, April 15, 1983).

The problem of thermal runaway absorption is unacceptable in a surgical laser system. As pointed out above, the absorption reduces the power which can be delivered to the patient. The heating of the gas also creates negative lensing which defocuses the beam and hinders proper surgical technique. In addition, the absorption can also heat the delivery apparatus which can cause burns to either the surgeon or the patient.

This effect has been observed by others prior to the invention herein but has been attributed to other factors, such as the optics being misaligned or out of focus. The latter explanation, while inadequate, was convenient since the delivery optics in surgical laser systems required articulated arms with many optical elements that can easily become, and often do, become misaligned. It is now recognized by the applicant that even small misalignments can and do greatly aggravate thermal runaway absorption in the purge gas.

Accordingly, it would be desirable to provide an improved laser system which prevents thermal runaway.

It is another object of the subject invention to provide an improved laser system for maximizing the power deliverable to a surgical site.

It is a further object of the subject invention to provide an improved surgical laser system which minimizes the absorption of the laser energy in the purge and insufflation gases.

It is still another object of the subject invention to provide an improved surgical laser system having a laser wavelength with enhanced absorption in tissue.

SUMMARY OF THE INVENTION

In accordance with these and other objects, the subject invention provides for an improved medical treatment laser system that minimizes undesirable absorption of laser energy along the beam delivery path. To achieve this goal the standard lasing medium is replaced with a different medium which produces a principal emission at wavelength shifted from the wavelength of the undesirable absorption.

In the preferred embodiment, the device includes a $CO_2$ laser for generating a laser beam. The $CO_2$ laser contains carbon dioxide gas as the lasing medium, typically mixed with non-lasing gases such as nitrogen and helium. A means is also provided for delivering the laser beam to the surgical site. In accordance with the subject invention, the improvement comprises replacing the standard $^{12}C^{16}O_2$ isotope of $CO_2$ in the laser with a different isotope. In the preferred embodiment, the selected isotope is $^{13}C^{16}O_2$. Where $^{13}C^{16}O_2$ is used as the gaseous lasing medium in a $CO_2$ laser, the principal wavelength generated is approximately 11.2 microns. This principal emission is shifted from the principal 10.6 micron line associated with the $^{12}C^{16}O_2$ isotope of $CO_2$.

The first significant advantage of this wavelength shift is that the standard $^{12}C^{16}O_2$ isotope of $CO_2$ absorbs little of the 11.2 micron energy. Therefore, where the $^{12}C^{16}O_2$ isotope of $CO_2$ is used for either the purge gas or insufflation gas, very little of the power of the $^{13}C^{16}O_2$ gas laser beam will be absorbed. Accordingly, the power that can be delivered to the surgical site can be maximized.

Another advantage of this change in the lasing medium is that the absorption coefficient in water of the 11.2 micron line of $^{13}C^{16}O_2$ is roughly 50% greater than the 10.6 line emitted by normal $CO_2$. A higher absorption coefficient permits lower energy thresholds for tissue cutting and ablation, which could lead to faster cutting. In addition, there would be a smaller layer of heat affected tissue which generally becomes denatured or necrotic.

The $^{13}C^{16}O_2$ isotope of $CO_2$ is readily available although it is relatively expensive. Fortunately, a $CO_2$ laser uses only a small amount of $CO_2$ gas at low pressure, and therefore, the incremental cost of manufacturing a $CO_2$ laser using the $^{13}C^{16}O_2$ isotope is very small. As noted above, most $CO_2$ lasers today are sealed systems rather than the earlier flowing gas systems, where this invention might have been more expensive to implement.

It is acknowledged that various isotopes of gases have been used in lasers and, in particular, isotopes of $CO_2$ have been used in gas lasers. In the history of laser development, virtually any gas which could be made to lase was tested. Isotopic lasers were particularly suited for spectroscopic studies where a wide range of laser lines is desirable. (See, for example, "Extension of $CO_2$ Laser Wavelength Range with Isotopes", Jacobs and Bowers, *Journal of Applied Physics*, Vol. 38, No. 6, p. 2692, May 1967, and "Determination of Laser Line Frequencies and Vibrational-Rotational Constants of $12C^{18}O_2$, $^{13}C^{16}O_2$ and $^{13}C^{18}O_2$ Isotopes from Measurements of CW Beat Frequencies with Fast HgCdTe Photodiodes and Microwave Frequency Counters", Freed et al., *Journal of Molecular Spectroscopy*, Vol. 49, p. 439 (1974)).

Isotopic $CO_2$ lasers were also investigated for communicating through the atmosphere. As noted above, it was recognized that where a $CO_2$ laser beam was transmitted over long distances, the small, but finite absorption of laser energy by the $CO_2$ in the atmosphere would add up to a significant degradation of beam power. However, this degradation was only a factor because of the long distances involved. This absorption effect has not been considered a problem in laser surgery by those skilled in the art because of the very short transmission distances encountered. The applicant has discovered that despite this short distance, absorption can be a problem, indeed a critical problem, created by the runaway phenomenon. This problem has been solved by using an isotope of $CO_2$ as the lasing medium to produce a critical improvement in laser surgery.

Further objects and advantages of the subject invention will become apparent from the following detailed description taken in conjunction with the drawings in which:

DETAILED DESCRIPTION OF THE PREFERRED EMBODIMENT

Figure 1:
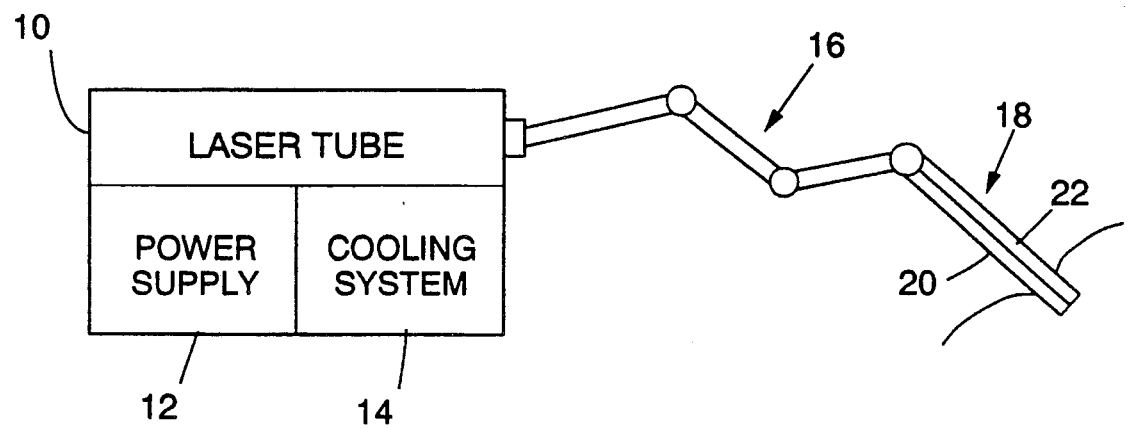
FIG. 1 is a schematic diagram of a surgical laser beam delivery system.

As noted above, the subject invention is particularly suited for use in $CO_2$ surgical laser systems. The assignee of the subject invention distributes a number of $CO_2$ surgical laser systems such as the XA30/CW, XA30/SP, XA40, XA50, XL40 and XL55. The XA50, for example, is a 50 watt laser system which can be operated in either the pulse mode or the continuous mode and includes a $CO_2$ laser. As shown in FIG. 1, the laser typically includes a sealed laser tube mounted in a housing. The associated power supply 12 and cooling system 14 is also self contained. The output from the laser is typically fed to an articulated arm 16 to allow the surgeon to deliver the beam to the surgical site. It is intended that the subject invention be utilized with any medical treatment laser system, the construction of which is well known to those skilled in the art.

In accordance with the subject invention, the standard laser system is modified to vary the lasing medium in the laser to utilize an isotope producing a principal wavelength having reduced absorption in the purge gas and/or enhanced absorption in the tissue to be treated. In the preferred embodiment, where a $CO_2$ laser is to be modified, the standard $^{12}C^{16}O_2$ isotope is replaced with $^{13}C^{16}O_2$. Other isotopes, such as $^{12}C^{18}O_2$ or $^{13}C^{18}O_2$ could also be used. However, it believed that $^{13}C^{16}O_2$ is the most advantageous, because there is less chance for isotope scrambling exchange inside the sealed laser tube, and because the 11.2 lasing wavelength is far removed from the absorption wavelength in standard $CO_2$.

The $^{13}C^{16}O_2$ isotope has an additional advantage in that the principal lasing wavelength (11.2 microns) has an increased coefficient of absorption in water. As noted above, the absorption of laser energy by water is the main mode for coupling the laser energy to human tissue. The coefficient k of absorption in water at 10.6 microns is approximately 890 $cm^{-1}$ while the absorption coefficient at 11.2 microns is approximately 1370 $cm^{-1}$, a 50% increase. (See Irvine and Pollack, *Icarus*, Vol. 8, No. 2, pp. 324-360, March 1968.) The significance of this enhanced absorption is that it permits lower energy thresholds for tissue cutting and ablation allowing faster and more accurate cutting. There would also be smaller areas of heat affected tissues which tend to become denatured and necrotic.

The other significant aspect of the use of an alternate isotope for the lasing medium in the gas laser is the ability to minimize absorption in the purge gas and insufflation gases. As noted in the background section above, the surgical laser beam is often delivered to the surgical site through a narrow air fiber delivery system. A number of companies manufacture air fiber delivery systems. The assignee of the subject invention distributes an air fiber delivery systems under the trademark EXCELITE TM. A generic example of such a delivery system is shown schematically as 18 in FIG. 1. This delivery system includes a channel 20 for delivering the beam from laser 10. A channel 22 is provided for circulating the purge gas.

As noted above, the most common purge gas in use today is standard $CO_2$. $CO_2$ is desirable because it can be efficiently disposed of by the circulatory and respiratory systems. The purge gas keeps all the optical surfaces inside the delivery system clean.

In the prior art, the standard $^{12}C^{16}O_2$ isotope was used in the $CO_2$ gas laser. This generated a laser beam with the predominate output wavelength at 10.6 microns. This output wavelength matched the absorption in the $CO_2$ purge gas.

Figure 2:
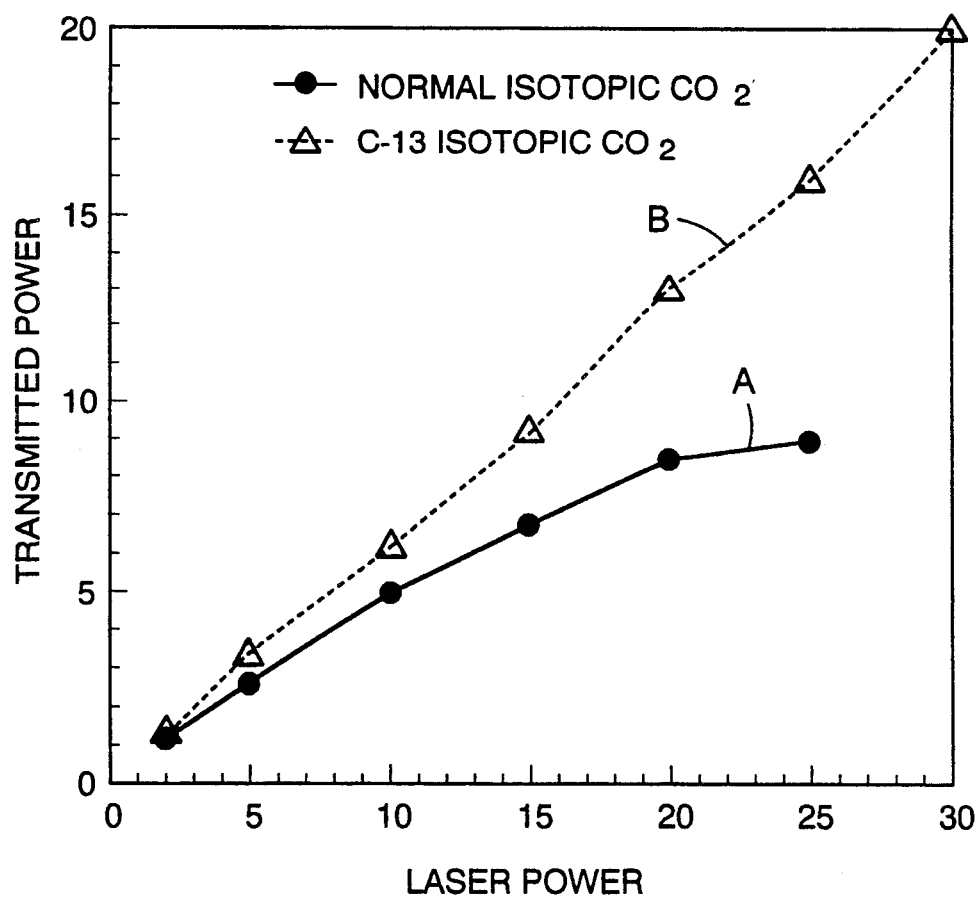
FIG. 2 is a graph comparing the laser power delivered to the input end of the delivery system with the power transmitted out of the delivery system using both normal ($^{12}C^{16}O_2$) and the $^{13}C^{16}O_2$ isotopes of $CO_2$.

Turning to the graph of FIG. 2, curve A illustrates the power which can be transmitted through a Coherent EXCELITE TM fiber delivery system where both the lasing medium and the purge gas are defined by the normal $^{12}C^{16}O_2$ isotope of $CO_2$. The data for this graph was taken during the development stage of Coherent's fiber delivery system. As can be seen, as the power levels increase, a rapid fall-off in the percentage of transmitted power occurs due to the absorption by the $CO_2$ purge gas. As mentioned above, this rapid fall-off has been attributed to the phenomenon of thermal runaway absorption in the purge gas in some cases aggregated by minor misalignments of optical elements. More specifically, at room temperature, there is a relatively low percentage of the $CO_2$ molecules which are in excited states. The particular excited vibrational state which would be responsible for absorbing the 10.6 micron line is denominated [1,0,0]. As the excited molecules absorb the energy from the laser beam, the gas in the restricted volume of the delivery system becomes rapidly heated, increasing the population of the higher energy $CO_2$ molecules, thereby increasing the resonant absorption by the molecules. This thermal runaway can prevent higher levels of power from ever being delivered to the patient. The heating will also create negative lensing which defocuses the beam and prevents proper delivery of the laser energy.

In accordance with the subject invention, the lasing medium is replaced with an isotope different from the isotope used in the purge gas. Curve B in FIG. 2 illustrates the result where the $^{13}C^{16}O_2$ isotope of $CO_2$ has been utilized as the lasing medium in the $CO_2$ laser. As can be seen, the percentage of the transmitted power delivered through air fiber remains relatively constant throughout the range of input powers. As can be seen from the graph, a substantial increase can be achieved in actual transmitted power, particularly at the higher power levels.

As noted above, in certain surgical operations such as laparoscopy, the surgeons will insufflate the surgical area with $CO_2$ gas. This gas, like the purge gas in the delivery system, will also absorb energy from the laser beam. In these procedures, it may be even more critical to provide an alternate lasing isotope so that the insufflation gas does not become heated inside the patient's body.

In summary, the subject invention defines an improved laser medical treatment system. In the preferred embodiment, the $^{13}C^{16}O_2$ isotope of $CO_2$ is used as the lasing medium in a $CO_2$ laser. The absorption of the output wavelengths by preferred purge gases and insufflation gases is substantially minimized by using an alternate isotope as the lasing medium. In addition, the $^{13}C^{16}O_2$ isotope produces a principal wavelength output which has increased absorption in water and, therefore, human tissue, to provide enhanced surgical capabilities.

While the subject invention has been described with reference to a preferred embodiment, other variations and modifications could be made therein by one skilled in the art without varying from the scope and spirit of the subject invention as defined by the appended claims.

I claim:

1. An improved medical treatment laser system including a gas laser for generating a beam of laser energy, a means for delivering the beam of laser energy to the medical treatment site, and a means for purging the delivering means using a purge gas, with the improvement comprising:

a gaseous lasing medium in the gas laser defined primarily by an isotope different from the isotope of the purge gas.

2. An improved medical treatment laser system as recited in claim 1 wherein the purge gas is $^{12}C^{16}O_2$ and the gaseous lasing medium is primarily a different isotope of $CO_2$.

3. An improved medical treatment laser system including a gas laser for generating a beam of laser energy, a means for delivering the beam of laser energy to the medical treatment site, and a means for providing a gas for insufflating the patient, with the improvement comprising:

a gaseous lasing medium in the gas laser defined primarily by an isotope different from the insufflation gas.

4. An improved medical treatment laser system as recited in claim 3 wherein the insufflation gas is $^{12}C^{16}O_2$ and the gaseous lasing medium is primarily a different isotope of $CO_2$.

5. In an improved $CO_2$ laser treatment apparatus including a $CO_2$ gas laser for generating a laser beam and a system means for delivering the beam to the patient, and wherein $CO_2$ purge gas is passed through the delivery system means, the improvement comprising:
a lasing medium in said gas laser defined primarily by an isotope of $CO_2$ different from the isotope used for the purge gas.

6. In an improved $CO_2$ laser treatment apparatus including a $CO_2$ gas laser for generating a laser beam and a means for delivering the beam to the patient, and a means for providing a gas for insufflating the patient, the improvement comprising:
a lasing medium in said gas laser defined primarily by an isotope of $CO_2$ different from the isotope used for the insufflation gas.

7. In an improved $CO_2$ gas laser treatment apparatus including a $CO_2$ gas laser for generating a laser beam and a system means for delivering the beam to the patient, and wherein purge gas defined by $^{12}C^{16}O_2$ is passed through the delivery system means, the improvement comprising:
a lasing medium in said laser defined primarily by $^{13}C^{16}O_2$.

8. In an improved $CO_2$ gas laser treatment apparatus including a $CO_2$ gas laser for generating a laser beam and a means for delivering the beam to the patient, a means for providing the $^{12}C^{16}O_2$ isotope of $CO_2$ gas for insufflating the patient, the improvement comprising:
a lasing medium in said laser defined by primarily $^{13}C^{16}O_2$.

9. A method of performing laser treatment on treatment site comprising;
generating a laser beam from a $CO_2$ laser;
directing the laser beam into a laser delivery system for delivering the beam to the treatment site;
purging the laser delivery system with a purge gas of $^{12}C^{16}O_2$ and wherein said step of generating a laser beam further includes utilizing as the primary lasing medium in the $CO_2$ laser an isotope of $CO_2$ different from $^{12}C^{16}O_2$.

10. A method as recited in claim 9 wherein the step of generating a laser beam includes exciting a lasing gain medium that is primarily $^{13}C^{16}O_2$.

11. A method for performing laser treatment on treatment site comprising;
generating a laser beam from a $CO_2$ laser;
directing the laser beam to the treatment site;
insufflating the treatment site with an insufflation gas of $^{12}C^{16}O_2$ and wherein said step of generating a laser beam further includes utilizing as the primary laser medium in the $CO_2$ laser an isotope of $CO_2$ different from $^{12}C^{16}O_2$.

12. A method as recited in claim 11 wherein step of generating a laser beam includes exciting a lasing gain medium that is primarily $^{13}C^{16}O_2$.

* * * * *